US008524654B2

(12) United States Patent
Blalock et al.

(10) Patent No.: US 8,524,654 B2
(45) Date of Patent: Sep. 3, 2013

(54) PROLYL ENDOPEPTIDASE INHIBITORS FOR REDUCING OR PREVENTING NEUTROPHILIC INFLAMMATION

(75) Inventors: J. Edwin Blalock, Birmingham, AL (US); Uros V. Djekic, Rockville, MD (US); Patricia L. Jackson, Moody, AL (US); Amit Gaggar, Homewood, AL (US); Brett Noerager, Birmingham, AL (US); Philip J. O'Reilly, Hoover, AL (US)

(73) Assignee: The UAB Research Foundation, Birmingham, AL (US)

( * ) Notice: Subject to any disclaimer, the term of this patent is extended or adjusted under 35 U.S.C. 154(b) by 552 days.

(21) Appl. No.: 12/601,216

(22) PCT Filed: May 21, 2008

(86) PCT No.: PCT/US2008/064404
§ 371 (c)(1),
(2), (4) Date: Jan. 7, 2010

(87) PCT Pub. No.: WO2008/144748
PCT Pub. Date: Nov. 27, 2008

(65) Prior Publication Data
US 2010/0167980 A1    Jul. 1, 2010

Related U.S. Application Data

(60) Provisional application No. 60/939,290, filed on May 21, 2007.

(51) Int. Cl.
*A61K 38/00* (2006.01)
*A61K 31/58* (2006.01)

(52) U.S. Cl.
USPC ............................................ 514/1.1; 514/176

(58) Field of Classification Search
None
See application file for complete search history.

(56) References Cited

U.S. PATENT DOCUMENTS

| | | | |
|---|---|---|---|
| 4,810,721 A | 3/1989 | Saitoh et al. | |
| 4,912,127 A | 3/1990 | Henning et al. | |
| 4,977,180 A | 12/1990 | Toda et al. | |
| 4,983,624 A | 1/1991 | Toda et al. | |
| 4,999,349 A | 3/1991 | Toda et al. | |
| 5,028,604 A | 7/1991 | Torizuka et al. | |
| 5,073,549 A | 12/1991 | Toda et al. | |
| 5,091,406 A | 2/1992 | Toda et al. | |
| 5,112,847 A | 5/1992 | Toda et al. | |
| 5,118,811 A | 6/1992 | Uchida et al. | |
| 5,198,458 A | 3/1993 | Higuchi et al. | |
| 5,254,550 A | 10/1993 | Toda et al. | |
| 5,262,431 A | 11/1993 | Toda et al. | |
| 5,407,950 A | 4/1995 | Okubo et al. | |
| 5,449,750 A | 9/1995 | Kimura et al. | |
| 5,506,256 A | 4/1996 | Kobayashi et al. | |
| 5,536,737 A | 7/1996 | Kobayashi et al. | |
| 5,661,167 A | 8/1997 | Peet et al. | |
| 5,756,763 A | 5/1998 | Takeuchi et al. | |
| 5,965,556 A | 10/1999 | Takeuchi et al. | |
| 6,875,851 B1 | 4/2005 | Travis et al. | |
| 6,878,751 B1 * | 4/2005 | Donnelly et al. | 514/733 |
| 7,304,086 B2 | 12/2007 | Schilling et al. | |
| 2004/0132639 A1 | 7/2004 | Ansorge et al. | |
| 2005/0014699 A1 | 1/2005 | Ansorge et al. | |
| 2007/0021360 A1 | 1/2007 | Nyce et al. | |

FOREIGN PATENT DOCUMENTS

| | | |
|---|---|---|
| EP | 0286928 | 4/1988 |
| EP | 0384341 | 8/1990 |
| WO | WO9012005 | 10/1990 |

OTHER PUBLICATIONS

Thorax, Aug. 1, 2007, vil 62, No. 8, 706-713, published online on Feb. 20, 2007.*
Marti et al., "Prolyl endopeptidase-mediated destruction of T cell epitopes in whole gluten: chemical and immunological characterization," J. Pharmacol. Exp. Ther. 312:19-26 (2005).
Matter et al., "Quantitative structure—activity relationship of human neutrophil collagenase (MMP-8) inhibitors using comparative molecular field analysis and x-ray structure analysis," J. Med. Chem. 42:1908-20 (2007).
Morain et al., "Pharmacodynamic and pharmacokinetic profile of S 17092, a new orally active prolyl endopeptidase inhibitor, in elderly healthy volunteers. A phase I study," Br. J. Clin. Pharmacol. 50:350-9 (2000).
Morain et al., "S 10792: A prolyl endopeptidase inhibitor as a potential therapeutic drug for memory impairment. Preclinical and clinical studies," CNS Drug Reviews 8:31-52 (2002).
Morain et al., "Psychotropic profile of S 17092, a prolyl endopeptidase inhibitor, using quantitative EEG in young healthy volunteers," Neuropsychobiology 55:176-83 (2007).
Nishikata et al., "Synthesis and structure of prolinal-containing peptides, and their use as specific inhibitors of prolyl endopeptidases," Chem. Pharm. Bull. 34:2931-6 (1986).
Nozaki et al., "Prolyl endopeptidase purified from granulomatous inflammation in mice," J. Cell. Biochem. 49:296-303 (1992).
O'Donnell et al., "Inflammatory cells in the airways in COPD," Thorax 61:448-54 (2006).
Olivo et al., "Representative aminopeptidases and prolyl endopeptidase from murine macrophages: comparative activity levels in resident and elicited cells," Biochem Pharmacol. 69:1441-50 (2005).
O'Reilly et al., "Interfering with extracellular matrix degradation to blunt inflammation," Curr. Opin. Pharma. 8:1-7 (2008).
Orlowski et al., "Proteolytic enzymes in bronchopulmonary lavage fluids: cathepsin B activity and prolyl endopeptidase," J. Lab. Clin. Med. 97:467-76 (1981).
Pfister et al., "Preliminary characterization of a polymorphonuclear leukocyte stimulant isolated from alkali-treated collagen," Invest. Ophthamol. Vis. Sci. 29:955-62 (1988).

(Continued)

*Primary Examiner* — Marcela M Cordero Garcia
*Assistant Examiner* — Kaipeen Yang
(74) *Attorney, Agent, or Firm* — Kilpatrick, Townsend & Stockton LLP

(57) ABSTRACT

Provided herein are methods for reducing or preventing neutrophilic inflammation in a subject comprising selecting a subject with or at risk for neutrophilic inflammation and administering to the subject an agent that inhibits the expression or activity of prolyl endopeptidase. Provided herein are also methods for treatment or prevention of diseases associated with neutrophilic inflammation.

28 Claims, 5 Drawing Sheets

(56) References Cited

OTHER PUBLICATIONS

Pfister et al., "Alkali-degraded cells generate respiratory burst stimulant for neutrophils," Cornea 12:155-60 (1993).
Pfister et al., "Alkali-degraded cornea generates low molecular weight chemoattractant for polymorphonuclear leukocytes," Invest. Ophthalmol. Vis. Sci. 34:2297-304 (1993).
Pfister et al., "Identification and synthesis of chemotactic tripeptides from alkali-degraded whole cornea. A study of N-acetyl-proline-glycine-proline and N-methyl-proline-glycine-proline," Invest. Ophthamol. Vis. Sci. 36:1306-16 (1995).
Pfister et al., "Injection of chemoattractants into mormal cornea: a model of inflammation after alkali injury," Invest. Ophthalmol. Vis. Sci. 39:1744-50 (1998).
Pfister et al., "Synthetic complementary peptides inhibit a neutrophil chemoattractant found in the alkali-injured cornea," Cornea 19:384-9 (2000).
Postlethwaite and Kang, "Collagen- and collagen peptide-induced chemotaxis of human blood monocytes," J. Exp. Med. 143:1299-1307 (1976).
Riley et al., "Neutrophil response following intratracheal instillation of collagen peptides into rat lungs," Exp. Lung. Res. 14:549-63 (1988).
Rosenblum et al., "Prolyl peptidases: a serine protease subfamily with high potential for drug discovery," Curr. Opin. Chem. Biol. 7:496-504 (2003).
Rowe et al., "Mechanisms of disease: cystic fibrosis," N. Engl. J. Med. 352:1992-2001 (2005).
Saito et al., "Synthesis and inhibitory activity of acyl-peptidyl-pyrrolidine derivatives toward post-proline cleaving enzyme: a study of subsite specificity," J. Enz. Inhib. Med. Chem. 5:51-75 (1991).
Schneider et al., "Effects of prolyl endopepdase inhibitor S 17092 on cognitive deficits in chronic low dose MPTP-treated monkeys," Neuropsychobiology 26:176-82 (2002).
Sedo et al., "Dipeptidyl peptidase IV, prolyl endopeptidase and cathepsin B activities in primary human lung tumors and lung parenchyma," J. Canc. Res. Clin. Oncol. 117:249-53 (1991).
Senior et al., "Chemotactic activity of elastin-derived peptides," J. Clin. Invest. 66:859-62 (1980).
Shan et al., "Structural and mechanistic analysis of two prolyl endopeptidases: role of interdomain dynamics in catalysis and specificity," Proc. Natl. Acad. Sci. USA 102:3599-604 (2005).
Shoji et al., "Depression of prolylendopeptidase activity in the delayed hypersensitive guinea pig skin lesion induced by bovine gamma-globulin," Biochem. Int. 18:1183-92 (1989).
Smith et al., "Specificity of inhibition of matrix metalloproteinase activity by doxycycline: relationship to structure of the enzyme," Arthritis Rheum. 42:1140-6 (1999).
Sternlicht and Werb, "How matrix metalloproteinases regulate cell behavior," Annu. Rev. Cell Dev. Biol. 17:463-516 (2001).
Toide et al., "JTP-4819: a novel prolyl endopeptidase inhibitor with potential as a cognitive enhancer," J. Pharma. Experiment. Therapeut. 274:1370-8 (1995).
Tsuru et al., "Thiazolidine derivatives as potent inhibitors specific for prolyl endopeptidase," J. Biochem. 104:580-6 (1988).
Van den Steen et al., "Neutrophil gelatinase B potentiates interleukin-8 tenfold by aminoterminal processing, whereas it degrades CTAP-III, PF-4, and GRO-a and leaves RANTES and MCP-2 intact," Blood 96:2673-81 (2000).
Walter, "Leucylglycinamide released from oxytocin by human uterine enzyme," Science 173:827-9 (1971).
Walter, "Partial purification and characterization of post-proline cleaving enzyme: enzymatic inactivation of neurohypophyseal hormones by kidney preparations of various species," Biochim. Biophys. Acta 422:138-58 (1976).
Weathington et al., "A novel peptide CXCR ligand derived from extracellular matrix degradation during airway inflammation," Nat. Med. 12:317-23 (2006).
Wilk and Orloeski, "Inhibition of rabbit brain prolyl endopeptidase by N-benzyloxycarbonyl-prolyl-prolinal, a transition state aldehyde inhibitor," J. Neurochem. 41:69-75 (1983).

Yoshimoto et al., "Postproline cleaving enzyme: identification as serine protease using active site specific inhibitors," Biochem. 16:2942 (1977).
Yoshimoto et al., "Post-proline cleaving enzyme (prolyl endopeptidase) from bovine brain," J. Biochem. 94:1179-90 (1983).
Angelastro et al., "Efficient preparation of peptidyl pentaflouroethly ketones," Tetrahedron Letters 33:3265-8 (1992).
Atack et al., "In vitro and in vivo inhibition of prolyl endopeptidase," Eur. J. Pharm. 205:157-63 (1991).
Atta-ur-Rahman et al., "Biodiversity as a source of new pharmacophores: a new theory of memory," Pure Appl. Chem. 77:75-81 (2005).
Baggionlini et al., "Human chemokines: an update," Ann. Rev. Immunol. 15:675-705 (1997).
Bakker et al., "Slow tight-binding inhibition of prolyl endopeptidase by benzyloxycarbonyl-prolyl-prolinal," Biochem. J. 271:559-62 (1990).
Bakker et al., "Novel in vitro and in vivo inhibitors of prolyl endopeptidase," Bioorganic & Medicinal Chem. Letts. 1:585-90 (1991).
Barelli et al., "S 17092-1, a highly potent, specific and cell permeant inhibitor of human proline endopeptidase," Biochem. Biophys. Res. Commun. 257:657-61 (1999).
Bellemere et al., "Effect of S 17092, a novel prolyl endopeptidase inhibitor, on substance P and α-melanocyte-stimulating hormone breakdown in the rat brain," J. Neurochem. 84:919-29 (2003).
Berton et al., "Involvement of fibronectin type II repeats in the efficient inhibition of gelatinases A and B by long-chain unsaturated fatty acids," J. Biol. Chem. 276:20458-65 (2001).
Cheng et al., "How can the mood stabilizer VPA limit both mania and depression?," Mol. Cell. Neurosci. 29:155-61 (2005).
Doring, "The role of neutrophil elastase on chronic inflammation," Am. J. Resp. Crit. Care Med. 150:S114-7 (1994).
Doring and Worlitzsch, "Inflammation in cystic fibrosis and its management," Paediatr. Respir. Rev. 1:101-6 (2000).
Emingil et al., "The effect of adjunctive low-dose doxycycline therapy on clinical parameters and gingival crevicular fluid matrix metalloproteinase-8 levels in chronic periodontitis," J. Periodontol. 75:106-15 (2004).
Foronjy et al., "Progressive adult-onset emphysema in transgenic mice expressing human MMP-1 in the lung," Am. J. Physiol. Lung Cell Mol. Physiol. 284:L727-37 (2003).
Friedman et al., "Prolyl endopeptidase: inhibition in vivo by N-benzyloxycarbonyl-prolyl-prolinal," J. Neurochem. 42:237-41 (1984).
Fryberg et al., "Possible role of MMP-9 in collagen fragmentation for bronchiolitis obliterans syndrome," American Thoracic Society Annual Meeting; San Fran., CA Abstract:A520 (2007).
Gaggar et al., "Matrix metalloprotease-9 dysregulation in lower airway secretions of cystic fibrosis patients," Am. J. Physiol. Lung Cell. Mol. Physiol. 293:L96-L104 (2007).
Gaggar et al., "Cystic fibrosis sputum generates chemotactic collagen fragments," American Thoracic Society Annual Meeting; San Fran., CA Abstract:A844 (2007).
Gaggar et al., "A novel proteolytic cascade generates an extracellular matrix-derived chemoattractant in chronic neutrophilic inflammation," J. Immunol. 180:5662-9 (2008).
Gass and Khosla, "Prolyl endopeptidases," Cell Mol. Life Sci. 64:345-55 (2007).
Haddox et al., "Bioactivity of peptide analogs of the neutrophil chemoattractant, N-acetyl-proline-glycine-proline," Invest. Opthalmol. Visual Sci. 40:2427-9 (1999).
Hautamaki et al., "Requirement for macrophage elastase for cigarette smoke-induced emphysema in mice," Science 277:2002-4 (1997).
Hoshino et al., "Bronchial subepithelial fibrosis and expression of matrix metalloproteinase-9 in asthmatic airway inflammation," J. Allergy Clin. Immunol. 102:783-8 (1998).
Je et al., "Sulfated chitooligosaccharides as prolyl endopeptidase inhibitor," Int. J. Biol. Macromol. 41:529-33 (2007).
Kamei et al., "Protective effect of eurystatins A and B, new prolyl endopeptidase inhibitors, on scopolamine-induced amnesia in rats," Japanese J. Pharma. 60:377-80 (1992).

Kakegawa et al., "Significant accumulations of cathespin B and prolylendopeptidase in inflammatory focus of delayed-type hypersensitivity induced by Mycobacterium tuberculosis in mice," Biochem. Biophys. Res. Commun. 316:78-84 (2004).

Kamori et al., "Activities of dipeptidyl peptidase II, dipeptidyl peptidase IV, proly endopeptidase and collagenase-like peptidase in synovial membrane from patients with rheumatoid arthritis and osteoarthritis," Biochem. Med. Metab. Biol. 45:154-60 (1991).

Kawabata et al., "ONO-5046, a novel inhibitor of human neutrophil elastase," Biochem. Biophys. Res. Commun. 177:814-20 (1991).

Koida and Walter, "Post-proline cleaving enzyme. Purification of this endopeptidase by affinity chromatography," J. Biol. Chem. 251:7593-9 (1976).

Laskin et al., "Chemotactic activity of collagen-like polypeptides for human peripheral blood neutrophils," J. Leukoc. Biol. 39:255-66 (1986).

Lee et al., "Plant phenolics as prolyl endopeptidase inhibitors," Arch. Pharm. Res. 30:827-33 (2007).

Lesser et al., "Cathepsin B and prolyl endopeptidase activity in rat peritoneal and alveolar macrophages. Simulation of peritoneal macrophages by saline lavage," J. Lab. Clin. Med. 101:327-34 (1983).

Levin et al., "The discovery of anthranilic acid-based MMP inhibitors. Part 2: SAR of the 5-position and P1¹ groups," Bioorg. Med. Chem. Lett. 11:2189-92 (2001).

Maes et al., "Lower serum prolyl endopeptidase enzyme activity in major depression: Further evidence that peptidases play a role in the pathophysiology of depression," Biol. Psychiatry 35:545-52 (1994).

Malik et al., "Matrix metalloprotease 9 activity enhances host susceptibility to pulmonary infection with type A and B strains of Francisella tularensis," J. Immunol. 178:1013-20 (2007).

Makinen et al., "An endo-acting proline-specific oligopeptidase from Treponema denticola ATCC 35405: evidence of hydrolysis of human bioactive peptides," Infect. Immun. 62:4938-47 (1997).

* cited by examiner

PROLYL ENDOPEPTIDASE INHIBITORS FOR REDUCING OR PREVENTING NEUTROPHILIC INFLAMMATION

CROSS-REFERENCE TO PRIORITY APPLICATIONS

This application claims priority to U.S. Provisional Application No. 60/939,290, filed May 21, 2007, which is incorporated herein by reference in its entirety.

STATEMENT REGARDING FEDERALLY SPONSORED RESEARCH

This invention was made with government support under Grant Nos. T32AI007493-13 and HL077783 awarded by the National Institutes of Health. The U.S. government has certain rights in the invention.

BACKGROUND

Neutrophils are important mediators in a variety of chronic inflammatory diseases affecting the airways, such as chronic obstructive pulmonary disease (COPD) and cystic fibrosis (CF). Neutrophil influx into these chronically inflamed airways propagates damage via multiple mechanisms, including oxidant injury and the release of proteolytic enzymes, leading to parenchymal lung injury and end-organ dysfunction.

The major chemoattractants for neutrophils in these conditions are glutamic acid-leucine-arginine-positive (ELR$^+$) CXC chemokines including IL-8, growth-related oncogene (GRO)-$\alpha$, GRO-$\beta$, and GRO-$\gamma$ in humans and KC and MIP-2 in mice. Nonspecific collagen-derived fragments have also been reported to induce neutrophil chemotaxis in murine models. Elastin fragments ending with proline-glycine have been shown as having the capacity to cause fibroblast and monocyte chemotaxis and, to a lesser degree, neutrophil chemotaxis.

Recent models of airway inflammation indicate that protease/antiprotease imbalance is a prime feature in several pulmonary diseases including COPD and CF. One class of proteases recently felt to play an important role in airway remodeling in lung disease are matrix metalloproteases (MMPs), a family of zinc containing endopeptidases with the capacity to degrade multiple components of the extracellular matrix. Recently, the presence and enhanced activity of discrete MMPs has been observed in the sputum of patients with CF, including MMP-8 and MMP-9 (Gaggar et al., *Am. J. Physiol* 293:L96-L104 (2007)). Despite recent evidence that implicates MMP-9 as involved in the generation of PGP, MMP-9 does not demonstrate the substrate specificity to liberate PGP directly from collagen by itself. Thus, one or more other proteases are likely involved. As such, the specific proteolytic mechanism for the release of this peptide from collagen is unknown.

SUMMARY

Provided herein are methods for reducing or preventing neutrophilic inflammation in a subject comprising selecting a subject with or at risk for neutrophilic inflammation and administering to the subject an agent that inhibits the expression or activity of prolyl endopeptidase. Provided herein are also methods for treatment or prevention of diseases associated with neutrophilic inflammation.

The details of one or more aspects are set forth in the accompanying drawings and the description below. Other features, objects, and advantages will be apparent from the description and drawings, and from the claims.

DETAILED DESCRIPTION

Figure 1A:
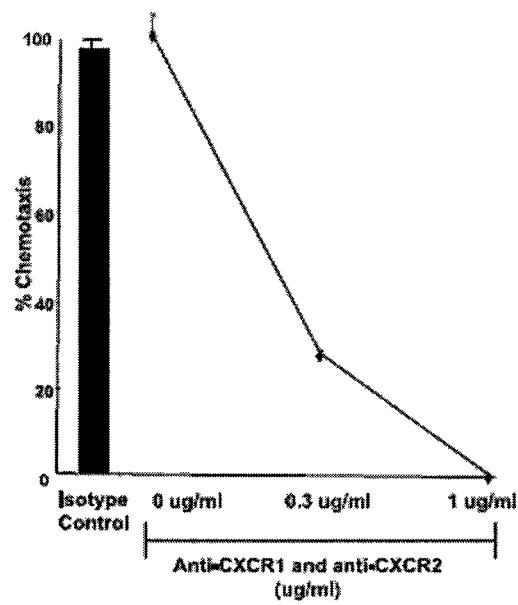
FIG. 1A shows that PGP acted via a CXCR-dependent mechanism to cause neutrophil chemotaxis. PMN was pretreated with CXCR1 and CXCR2 Abs or IgG2a isotype control Ab (2 µg/ml) for 1 h at 22° C. PGP (at 10 µg/ml) was placed in the bottom of chemotaxis plate. The isotype Ab demonstrated no change in neutrophil chemotaxis compared with untreated cells (■). However, at 1 µg/ml concentration of each CXCR Ab, PGP chemotaxis is completely blocked (*, p<0.01 compared with no Ab and isotype Ab control).

A role for a specific collagen-derived peptide, N-acetylated proline-glycine-proline (N-α-PGP), in neutrophilic lung inflammation has been described (Weathington et al., *Nat. Med.* 12:317-323 (2006)). N-α-PGP, via structural homology to most ELR+ CXC chemokines, acts as neutrophil chemoattractants through CXCR1 and CXCR2 on neutrophils. This CXC ligand demonstrates the ability to not only induce neutrophil chemotaxis but also to induce superoxide release from neutrophils via CXCR1 binding. The cellular kinetic response to aerosolized LPS administration to mice demonstrates that initial neutrophil influx is dependent on traditional ELR+ chemokines (KC and MIP-2) but is maintained and augmented by N-α-PGP until neutrophils are cleared from the airways, concomitant with declining N-α-PGP levels in the airway.

Nonacetylated proline-glycine-proline (PGP) has been previously described as a neutrophil chemoattractant in vitro, although it is four to seven times less potent than N-α-PGP (Haddox et al., *Invest. Opthalmol. Visual Sci.* 40:2427-9 (1999)). Recently, the presence of PGP as a prominent neutrophil chemoattractant in a murine model of pneumonic tularemia has been described (Malik et al., *J. Immunol.* 178: 1013-1020 (2007)), although the mechanisms for inducing chemotaxis are not known. In addition, although N-α-PGP has been reported from clinical disease samples, PGP has not been reported in clinical samples. Despite the presence of PGP-containing peptides and other structural proteins in animal models of inflammation, no specific ECM-derived peptide has been consistently shown as a biomarker in clinical disease. Although the biological properties of some of these peptides are becoming increasingly understood, the specific mechanism of generation of these peptides remains unclear, although proteolytic enzymes are thought to play a role (Malik et al., *J. Immunol.* 178:1013-1020 (2007); Hautamaki et al., *Science* 277:2002-4 (1997)).

The present disclosure describes the mechanism of PGP-induced neutrophil chemotaxis, the specific proteolytic mechanisms involved in PGP generation from collagen, and their importance in neutrophilic inflammation. Specifically, mass spectrometry (MS) technique was used to simultaneously detect both N-α-PGP and PGP in clinical samples. As described in the examples below, the presence of PGP containing peptides was observed in significantly increased quantities in the sputum of CF individuals compared with healthy subjects. Using an ex vivo system, the examples below also demonstrate the capacity of CF sputum to generate PGP from intact collagen. The proteolytic system involved in PGP generation is described herein as a two-step process using the coordinated efforts of MMPs (MMP-8 and MMP-9) and prolyl endopeptidase (PE), a serine protease herein described for the first time with a role related to airway and neutrophilic inflammation. The examples below also show that PGP levels are elevated during CF exacerbation and that inhibition of MMP-8, MMP-9, and PE blocks ex vivo generation of PGP by CF sputum, pointing to a role of these inhibitors as therapeutics in neutrophilic diseases, including CF.

Thus, provided herein is a method for reducing or preventing neutrophilic inflammation in a subject comprising selecting a subject with or at risk for neutrophilic inflammation and administering to the subject an agent that inhibits the expression or activity of prolyl endopeptidase. Optionally, the method further comprises administering to the subject an agent that inhibits the expression or activity of a matrix metalloprotease (MMP). Optionally, the MMP is MMP-8 or MMP-9. Optionally, the subject has or is at risk for a disease associated with neutrophilic inflammation. As used here, neutrophilic inflammation means inflammation mediated, at least in part, by the function and/or activity of neutrophilic cells, including, but not limited to, the release of mediators by neutrophilic cells, the death of neutrophilic cells and the activity of cells and processes activated or inhibited by the function of neutrophilic cells. Optionally, the neutrophilic inflammation is chronic neutrophilic inflammation. Diseases associated with neutrophilic inflammation include, but are not limited to asthma, chronic obstructive pulmonary disease (COPD), cystic fibrosis (CF), pulmonary transplantation rejection, chronic bronchitis, emphysema, bronchiectasis, bronchiolitis obliterans syndrome (BOS), interstitial pneumonia, pulmonary fibrosis, bacterial infection and viral infection. Optionally, the bacterial or viral infection is a bacterial or viral lung infection.

As used herein, prolyl endopeptidase (PE) refers to PE and homologs, variants and isoforms thereof. There are a variety of sequences that are disclosed on Genbank, at www.pubmed.gov, and these sequences and others are herein incorporated by reference in their entireties as well as for individual subsequences contained therein. For example, the amino acid and nucleic acid sequences of human PE can be found at GenBank Accession Nos. NP_002717.3 and NM_002726.3, respectively.

Provided herein are PE inhibitors for the treatment or prevention of neutrophilic inflammation and diseases associated with neutrophilic inflammation. Inhibitors of PE include, but are not limited to, inhibitory peptides, drugs, functional nucleic acids and antibodies.

Inhibitors of PE include inhibitory peptides or polypeptides. As used herein, the term peptide, polypeptide, protein or peptide portion is used broadly herein to mean two or more amino acids linked by a peptide bond. Protein, peptide and polypeptide are also used herein interchangeably to refer to amino acid sequences. The term fragment is used herein to refer to a portion of a full-length polypeptide or protein. It should be recognized that the term polypeptide is not used herein to suggest a particular size or number of amino acids comprising the molecule and that a peptide of the invention can contain up to several amino acid residues or more. Peptides can be tested for their ability to inhibit PE by methods known to those of skill in the art, such as, for example, phage display and yeast two-hybrid assays. Inhibitory peptides of PE include, but are not limited to, SNA-115 and SNA-115T as described in U.S. Pat. No. 5,449,750, which is incorporated by reference herein in its entirety. Inhibitory peptides also include dominant negative mutants of PE. Dominant negative mutations (also called antimorphic mutations) have an altered phenotype that acts antagonistically to the wild-type or normal protein. Thus, dominant negative mutants of PE act to inhibit the normal PE protein. Such mutants can be generated, for example, by site directed mutagenesis or random mutagenesis. Proteins with a dominant negative phenotype can be screened for using methods known to those of skill in the art, for example, by phage display. Such peptides are selected based on their ability to inhibit PE.

Nucleic acids that encode the aforementioned peptide sequences are also disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. A wide variety of expression systems may be used to produce peptides as well as fragments, isoforms, and variants.

Suitable inhibitors of prolyl endopeptidase (PEP) also include, but are not limited to, chemical derivatives of proline or small peptides containing terminal prolines. For example, inhibitors of PE include, but are not limited to, the compounds described in U.S. Pat. Nos. 5,965,556; 5,756,763; 5,661,167; 5,536,737; 5,506,256; 5,499,750; 5,407,950; 5,262,431; 5,254,550; 5,198,458; 5,118,811; 5,112,847, 5,091,406; 5,073,549; 5,028,604, 4,999,349; 4,983,624; and 4,977,180. Benzyloxycarbonyl-prolyl-prolinal has been shown to be a specific transition state inhibitor of the enzyme (Wilk and Orloeski, J. Neurochem., 41, 69 (1983); Friedman, et al., Neurochem., 42, 237 (1984)). N-terminal substitutions of L-proline or L-prolylpyrrolidine (Atack et al., Eur. J. of Pharm., 205, 157-163 (1991); and EP 0 384 341), as well as variations of N-benzyloxycarbonyl (Z) dipeptides containing prolinal at the carboxy terminus have been synthesized as prolyl endopeptidase inhibitors (Nishikata et al., Chem. Pharm. Bull. 34(7), 2931-2936 (1986); Baker et al., Bioorganic & Medicinal Chem. Letts., 1(11), 585-590 (1991)). Thioproline, thiazolidine, and oxopyrrolidine substitutions of the core structure have been reported to inhibit prolyl endopeptidase (Tsuru et al., J. Biochem., 94, 1179 (1988); Tsuru et al., J. Biochem., 104, 580-586 (1988); Saito et al., J. Enz. Inhib. 5, 51-75 (1991); and WO 90/12005). Similarly, various modifications of the carboxy terminal proline have been made, including various fluorinated ketone derivatives (EP Patent No. 4 912 127). General syntheses of fluorinated ketone derivatives has been described (Angelastro et al., Tetrahedron Letters 33(23), 3265-3268 (1992)). Other compounds such as chloromethyl ketone derivatives of acyl-proline or acylpeptide-proline (Z-Gly-Pro-CH$_2$Cl) have been demonstrated to inhibit PE by alkylating the enzyme's active site (Yoshimoto et al., Biochemistry 16, 2942 (1977)). EP Patent No. 0 286 928, discloses 2-acylpyrrolidine derivatives useful as propyl endopeptidase inhibitors. S 17092, which was originally developed for treatment of neurologic disorders (Bellemere et al., J. Neurochem. 84(5):919-29 (2003)), has also been shown to specifically inhibit PE (Barelli et al., Biochem. Biophys. Res. Commun. 257(3):657-61 (1999)).

Other inhibitors of PE include those described in U.S. Pat. No. 5,536,737; proline derivatives (U.S. Pat. No. 5,506,256); pyrrolidineamide derivatives (U.S. Pat. No. 4,810,721); prolinal derivatives (U.S. Pat. No. 4,983,624); eurystatin (Hideo Kamei, et al., "Protective Effect of Eurystatins A and B, New Prolyl Endopeptidase Inhibitors, on Scopolamine-Induced Amnesia in Rats," The Japanese Journal of Pharmacology Vol. 60, No. 4, pp. 377-380 (1992)); JTP-4819 (Toide et al., "JTP-4819: a novel prolyl endopeptidase inhibitor with potential as a cognitive enhancer," Journal of Pharmacology And Experimental Therapeutics, Vol. 274, Issue 3, pp. 1370-1378, (1995)); sulfated chitooligosaccharides (Je et al., "Sulfated chitooligosaccharides as prolyl endopeptidase inhibitor," Int J Biol Macromol. 41(5):529-33 (2007)).

Inhibitors of PE include plant phenolics (Lee et al., "Plant phenolics as prolyl endopeptidase inhibitors," Arch Pharm Res., 30(7):827-33 (2007)) such as, for example, 1,2,3-trigalloyl glucopyranoside, 1,2,6-trigalloyl glucopyranoside, 1,2,3,4,6-pentagalloyl gluco-pyranoside, 1,2,6-trigalloyl alloside, 1,3,6-trigalloyl alloside, 1,2,3,6-tetragalloyl alloside, acetonyl geraniin, corilagin, elaeocarpusin, euphorscopin, geraniin, helioscopin B, helioscopinin A, helioscopinin B, jolkinin, macranganin, rugosin E, supinanin, and teracatain.

Also provided herein are functional nucleic acids that inhibit expression of PE. Such functional nucleic acids include but are not limited to antisense molecules, aptamers, ribozymes, triplex forming molecules, RNA interference (RNAi), and external guide sequences. Thus, for example, a small interfering RNA (siRNA) could be used to reduce or eliminate expression of PE. Functional nucleic acids are nucleic acid molecules that have a specific function, such as binding a target molecule or catalyzing a specific reaction.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Representative examples of how to make and use aptamers to bind a variety of different target molecules can be found in, for example, U.S. Pat. Nos. 5,476,766 and 6,051,698.

Ribozymes are nucleic acid molecules that are capable of catalyzing a chemical reaction, either intramolecularly or intermolecularly. There are a number of different types of ribozymes that catalyze nuclease or nucleic acid polymerase type reactions which are based on ribozymes found in natural systems, such as hammerhead ribozymes, hairpin ribozymes and tetrahymena ribozymes). There are also a number of ribozymes that are not found in natural systems, but which have been engineered to catalyze specific reactions de novo (for example, but not limited to U.S. Pat. Nos. 5,807,718, and 5,910,408). Ribozymes may cleave RNA or DNA substrates. Representative examples of how to make and use ribozymes to catalyze a variety of different reactions can be found in U.S. Pat. Nos. 5,837,855; 5,877,022; 5,972,704; 5,989,906; and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. Representative examples of how to make and use triplex forming molecules to bind a variety of different target molecules can be found in U.S. Pat. Nos. 5,650,316; 5,683,874; 5,693,773; 5,834,185; 5,869,246; 5,874,566; and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. Representative examples of how to make and use EGS molecules to facilitate cleavage of a variety of different target molecules be found in U.S. Pat. Nos. 5,168,053; 5,624,824; 5,683,873; 5,728,521; 5,869,248; and 5,877,162.

Gene expression can also be effectively silenced in a highly specific manner through RNA interference (RNAi). Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit (Ambion, Austin, Tex.).

Proteins that inhibit PE also include antibodies with antagonistic or inhibitory properties. In addition to intact immunoglobulin molecules, fragments, chimeras, or polymers of immunoglobulin molecules are also useful in the methods taught herein, as long as they are chosen for their ability to inhibit PE. The antibodies can be tested for their desired activity using in vitro assays, or by analogous methods, after which their in vivo therapeutic or prophylactic activities are tested according to known clinical testing methods.

The term antibody is used herein in a broad sense and includes both polyclonal and monoclonal antibodies. Monoclonal antibodies can be made using any procedure that produces monoclonal antibodies. For example, disclosed monoclonal antibodies can be prepared using hybridoma methods, such as those described by Kohler and Milstein, Nature, 256: 495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

As used throughout, antibody fragments include Fv, Fab, Fab' or other antigen binding portion of an antibody. Digestion of antibodies to produce fragments thereof, e.g., Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

The antibody fragments, whether attached to other sequences, also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curt Opin. Biotechnol. 3:348-354, 1992).

As used herein, the term antibody or antibodies can also refer to a human antibody and/or a humanized antibody. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1): 86 95, 1991). Human antibodies (and fragments thereof) can also be produced using phage display libraries (Hoogenboom et al., J. Mol. Biol., 227:381, 1991; Marks et al., J. Mol. Biol., 222: 581, 1991). The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551 255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ line mutant mice results in complete inhibition of endogenous antibody production, and the successful transfer of the human germ line antibody gene array into such germ line mutant mice results in the production of human antibodies upon antigen challenge.

Antibody humanization techniques generally involve the use of recombinant DNA technology to manipulate the DNA sequence encoding one or more polypeptide chains of an antibody molecule. Accordingly, a humanized form of a non human antibody (or a fragment thereof) is a chimeric antibody or antibody chain that contains a portion of an antigen binding site from a non-human (donor) antibody integrated into the framework of a human (recipient) antibody. Fragments of humanized antibodies are also useful in the methods taught herein. Methods for humanizing non human antibodies are well known in the art. For example, humanized antibodies can be generated according to the methods of Winter and co workers (Jones et al., Nature, 321:522 525 (1986), Riechmann et al., Nature, 332:323 327 (1988), Verhoeyen et al., Science, 239:1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5, 939,598 (Kucherlapati et al.), U.S. Pat. No. 6,130,364 (Jakobovits et al.), and U.S. Pat. No. 6,180,377 (Morgan et al.).

Methods of screening for agents that inhibit the activity of PE are provided. Such a screening method comprises the steps of providing a cell that expresses PE, contacting the cell with a candidate agent to be tested and determining whether the candidate agent prevents the expression or activation of PE. Another method of screening for agents that inhibit the activity of PE comprises the steps of providing a sample comprising PE, contacting the sample with a candidate agent to be tested and determining whether the candidate agent prevents the activation of PE. The provided cells that express PE can be made by infecting the cell with a virus comprising PE wherein the PE is expressed in the cell following infection. The cell can also be a prokaryotic or an eukaryotic cell that has been transfected with a nucleotide sequence encoding PE or a variant or a fragment thereof, operably linked to a promoter. Using DNA recombination techniques well known by the one skill in the art, protein encoding DNA sequences can be inserted into an expression vector, downstream from a promoter sequence. Alternatively, the cell expressing PE optionally naturally expresses PE.

Such methods allow one skilled in the art to select candidate agents that inhibit PE expression or activity. Such agents may be useful as active ingredients included in pharmaceutical compositions. Methods for determining whether the candidate agent prevents expression or activation of PE are known. The assay can be, for example, a proteolytic assay or one of the provided methods described in the examples below.

Provided herein are also methods of determining whether a subject has or is at risk for neurotrophic inflammation or a disease associated with neutrophilic inflammation. Specifically, provided is a method of determining whether a subject has or is at risk for neutrophilic inflammation or a disease associated with neutrophilic inflammation, comprising obtaining a biological sample from the subject, and determining the level of expression or activity of PE in the sample, wherein an increase in expression or activity of PE as compared to a control indicates the subject has or is at risk for neutrophilic inflammation or a disease associated with neutrophilic inflammation. Optionally, the methods further comprise administering to the subject an agent that inhibits the expression or activity or prolyl endopeptidase if the subject has neutrophilic inflammation or a disease associated with neutrophilic inflammation. Such agents include, but are not limited to, the agents specifically described herein.

As used herein a biological sample which is subjected to testing is a sample derived from a subject and includes, but is not limited to, any cell, tissue or biological fluid. Examples of bodily fluids include, but are not limited to, sputum, whole blood, serum, saliva, tissue infiltrate, pleural effusions, lung lavage fluid, bronchoalveolar lavage fluid, and the like. The biological fluid may be a cell culture medium or supernatant of cultured cells. For example, the sample can be a blood sample or a sputum sample.

An increase in expression or activity of PE as compared to a control means that the level of expression or activity of PE is at least 1.5 times higher in the biological sample from a subject being tested than in a control sample. As used throughout, higher, increases, enhances or elevates as compared to a control refer to increases above a control. For example, a control level can be the level of expression or activity in a control sample in the absence of a stimulus. A control sample as used herein includes a sample from a subject without neutrophilic inflammation or a disease associated with neutrophilic inflammation, such as, for example, cystic fibrosis.

Assay techniques that can be used to determine levels of expression or activity in a sample are known. Such assay methods include, but are not limited to, radioimmunoassays, reverse transcriptase PCR(RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Assays also include, but are not limited to, competitive and non-competitive assay systems using techniques such as radioimmunoassays, enzyme immunoassays (EIA), enzyme linked immunosorbent assay (ELISA), sandwich immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays. For examples of immunoassay methods, see U.S. Pat. Nos. 4,845,026 and 5,006,459.

In an ELISA assay, an antibody is prepared, if not readily available from a commercial source, specific to an antigen, such as, for example, PE. In addition, a reporter antibody generally is prepared which binds specifically to the antigen. The reporter antibody is attached to a detectable reagent such as a radioactive, fluorescent or enzymatic reagent, for example horseradish peroxidase enzyme or alkaline phosphatase. To carry out the ELISA, antibody specific to antigen is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time the antigen binds to the specific antibody attached to the polystyrene dish. Unbound sample is washed out with buffer. A reporter antibody specifically directed to the antigen and linked to a detectable reagent such as horseradish peroxidase is placed in the dish resulting in binding of the reporter antibody to any antibody bound to the antigen. Unattached reporter antibody is then washed out. Reagents for peroxidase activity, including a colorimetric substrate are then added to the dish. Immobilized peroxidase, linked to antibodies, produces a colored reaction product. The amount of color developed in a given time period is proportional to the amount of antigen present in the sample. Quantitative results typically are obtained by reference to a standard curve.

Optionally, a genetic sample from the biological sample can be obtained. The genetic sample comprises a nucleic acid, preferably RNA and/or DNA. For example, in determining the expression of genes mRNA can be obtained from the biological sample, and the mRNA may be reverse transcribed into cDNA for further analysis. Alternatively, the mRNA itself is used in determining the expression of genes.

A genetic sample may be obtained from the biological sample using any techniques known in the art (Ausubel et al. Current Protocols in Molecular Biology (John Wiley & Sons, Inc., New York, 1999); Molecular Cloning: A Laboratory Manual, 2nd Ed., ed. by Sambrook, Fritsch, and Maniatis (Cold Spring Harbor Laboratory Press: 1989); Nucleic Acid Hybridization (B. D. Hames & S. J. Higgins eds. 1984)). The nucleic acid may be purified from whole cells using DNA or RNA purification techniques. The genetic sample may also be amplified using PCR or in vivo techniques requiring subcloning. The genetic sample can be obtained by isolating mRNA from the cells of the biological sample and reverse transcribing the RNA into DNA in order to create cDNA (Khan et al. Biochem. Biophys. Acta 1423:17 28, 1999).

Once a genetic sample has been obtained, it can be analyzed. The analysis may be performed using any techniques known in the art including, but not limited to, sequencing, PCR, RT-PCR, quantitative PCR, restriction fragment length polymorphism, hybridization techniques, Northern blot, microarray technology, DNA microarray technology, and the like. In determining the expression level of a gene or genes in a genetic sample, the level of expression may be normalized by comparison to the expression of another gene such as a well known, well characterized gene or a housekeeping gene. For example, reverse-transcriptase PCR (RT-PCR) can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA.

Hybridization to clones or oligonucleotides arrayed on a solid support (i.e., gridding) can be used to both detect the expression of and quantitate the level of expression of that gene. In this approach, a cDNA encoding an antigen is fixed to a substrate. The substrate may be of any suitable type including but not limited to glass, nitrocellulose, nylon or plastic. At least a portion of the DNA encoding the antigen is attached to the substrate and then incubated with the analyte, which may be RNA or a complementary DNA (cDNA) copy of the RNA, isolated from the sample of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The herein provided compositions are administered in vitro or in vivo in a pharmaceutically acceptable carrier. Optionally, the composition further comprises an adjuvant. Optionally, compositions comprising the immunogenic polypeptide contain one or more additional immunogens.

By pharmaceutically acceptable carrier is meant a material that is not biologically or otherwise undesirable, i.e., the material is administered to a subject, e.g., along with the immunogenic polypeptide, without causing any undesirable biological effects or interacting in a deleterious manner with any of the other components of the pharmaceutical composition in which it is contained. The carrier is selected to minimize any degradation of the active ingredient and to minimize any adverse side effects in the subject.

Suitable carriers and their formulations are described in *Remington: The Science and Practice of Pharmacy*, $21^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained release preparations such as semipermeable matrices of solid hydrophobic polymers containing the immunogenic polypeptides. Matrices are in the form of shaped articles, e.g., films, liposomes or microparticles. Certain carriers may be more preferable depending upon, for instance, the route of administration and concentration of composition being administered. Carriers are those suitable for administration of the agent, e.g., polypeptide, to humans or other subjects.

The compositions are administered in a number of ways depending on whether local or systemic treatment is desired, and on the area to be treated. The compositions are administered via any of several routes of administration, including, topically, orally, parenterally, intravenously, intraperitoneally, intramuscularly, subcutaneously, intracavity, transdermally, intrahepatically, intracranially, nebulization/inhalation, or by instillation via bronchoscopy. Optionally, the composition is administered by oral inhalation, nasal inhalation or intranasal mucosal administration. Administration of the compositions by inhalant can be through the nose or mouth via delivery by a spraying or droplet mechanism. For example, in the form of an aerosol.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

As used herein, topical intranasal administration means delivery of the compositions into the nose and nasal passages through one or both of the nares and can comprise delivery by a spraying mechanism or droplet mechanism, or through aerosolization of the nucleic acid or vector. Administration of the compositions by inhalant is through the nose or mouth via delivery by a spraying or droplet mechanism. Delivery is optionally directly to any area of the respiratory system (e.g., lungs) via intubation.

Formulations for topical administration include ointments, lotions, creams, gels, drops, suppositories, sprays, liquids and powders. Conventional pharmaceutical carriers, aqueous, powder or oily bases, thickeners and the like are optionally necessary or desirable.

Compositions for oral administration include powders or granules, suspensions or solutions in water or non-aqueous media, capsules, sachets, or tablets. Thickeners, flavorings, diluents, emulsifiers, dispersing aids or binders are optionally desirable.

The provided compositions can be administered in combination with one or more other therapeutic or prophylactic regimens. Thus, the provided methods can further comprise the step of administering a second therapeutic agent to the subject. As used throughout, a therapeutic agent is a compound or composition effective in ameliorating a pathological condition. Illustrative examples of therapeutic agents include, but are not limited to, anti-viral agents, anti-opportunistic agents, antibiotics, and immunosuppressive agents. Optionally, the provided methods further include administering a matrix metalloprotease (MMP) inhibitor. Suitable MMP inhibitors include inhibitors of MMP-8 or MMP-9. Inhibitors of MMP-8 and MMP-9 are known and include, but are not limited to, the inhibitors listed in Table 1 in the examples below.

Antibacterial agents that may be administered with the provided compositions include, but are not limited to, amoxicillin, aminoglycosides, beta-lactam (glycopeptide), beta-lactamases, clindamycin, chloramphenicol, cephalosporins, ciprofloxacin, erythromycin, fluoroquinolones, macrolides, metronidazole, penicillins, quinolones, ritampin, streptomycin, sulfonamide, tetracyclines, trimethoprim, trimethoprim-sulfamthoxazole, and vancomycin.

Immunosuppressive agents, that may be administered in combination with the provided compositions include, but are not limited to steroids, cyclosporine, cyclosporine analogs, cyclophosphamide methylprednisone, prednisone, azathioprine, FK-506 (Fujisawa Pharmaceuticals, Deerfield, Ill.), 15 deoxyspergualin, and other immunosuppressive agents that act by suppressing the function of responding immune cells (including, for example, T cells), directly (e.g., by acting on the immune cell) or indirectly (by acting on other mediating cells). Immunosuppresive agents also include, ORTHOCLONE® (OKT3) (Ortho Biotech, Raritan, N.J.), SANDIMMUNE® ORAL (cyclosporine) (Sandoz Pharmaceuticals, Hanover, N.J.), PROGRAF® (tacrolimus) (Fujisawa Pharmaceuticals, Deerfield, Ill.), CELLCEPT® (mycophenolate) (Roche Pharmaceuticals, Nutley, N.J.), azathioprine, glucorticosteroids, and RAPAMUNE® (sirolimus) (Wyeth, Collegeville, Pa.). The immunosuppressants in combination with the provided inhibitors may be used to prevent rejection of organ transplantation.

Anti-inflammatory agents that may be administered with the provided compositions include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, ninesulide, orgotein, oxaceprol, paranyline, perisoxal, pifoxime, proquazone, proxazole, and tenidap.

Any of the aforementioned second therapeutic agents or treatment regimes can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to either concomitant, simultaneous, or sequential administration of two or more agents.

The terms effective amount and effective dosage are used interchangeably. The term effective amount is defined as any amount necessary to produce a desired physiologic response. Effective amounts and schedules for administering the compositions are determined empirically. The dosage ranges for the administration of the compositions are those large enough to produce the desired effect in which the symptoms or disorder are affected. The dosage is not so large as to cause substantial adverse side effects, such as unwanted cross-reactions, anaphylactic reactions, and the like. Generally, the dosage varies with the age, condition, sex, type of disease and extent of the disease in the patient, route of administration, or whether other drugs are included in the regimen, and is determined by one of skill in the art. The dosage is optionally adjusted by the individual physician in the event of any contraindications. Doses are administered in one or more dose administrations daily, for one or several days.

As used throughout, by a subject is meant an individual. Thus, the subject can include, for example, domesticated animals, such as cats and dogs, livestock (e.g., cattle, horses, pigs, sheep, and goats), laboratory animals (e.g., mice, rabbits, rats, and guinea pigs) mammals, non-human mammals, primates, non-human primates, rodents, birds, reptiles, amphibians, fish, and any other animal. The subject can be a mammal such as a primate or a human. The term subject also includes individuals of different ages. Thus, a subject includes an infant, child, teenager or adult.

There are a variety of sequences related to, for example, prolyl endopeptidase (PE; EC 3,4,21,26), at www.pubmed.gov and these sequences and others are herein incorporated by reference in their entireties as well as for individual subsequences contained therein.

As used herein the terms treatment, treat or treating refers to a method of reducing the effects of a disease or condition or symptom of the disease or condition. Thus in the disclosed method treatment can refer to a 10%, 20%, 30%, 40%, 50%, 60%, 70%, 80%, 90% or 100% reduction in the severity of an established disease or condition or symptom of the disease or condition. For example, a method for treating a disease is considered to be a treatment if there is a 10% reduction in one or more symptoms of the disease in a subject as compared to control. Thus the reduction can be a 10, 20, 30, 40, 50, 60, 70, 80, 90, 100% or any percent reduction in between 10 and 100 as compared to native or control levels. It is understood that treatment does not necessarily refer to a cure or complete ablation of the disease, condition or symptoms of the disease or condition.

As used herein, the terms prevent, preventing and prevention of a disease or disorder refers to an action, for example, administration of a therapeutic agent, that occurs before a subject begins to suffer from one or more symptoms of the disease or disorder, which inhibits or delays onset of the severity of one or more symptoms of the disease or disorder. As used herein, references to decreasing, reducing, or inhibiting include a change of 10, 20, 30, 40, 50, 60, 70, 80, 90 percent or greater as compared to a control level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if an inhibitor is disclosed and discussed and a number of modifications that can be made to a number of molecules including the inhibitor are discussed, each and every combination and permutation of the inhibitor, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

Example 1
Role of Chemotactic Peptide Proline-Glycine-Proline (PGP) in Neutrophilic Inflammation Materials and Methods CF subjects. All subjects carried the diagnosis of CF based on accepted diagnostic criteria, including a minimum of two clinical features consistent with the diagnosis and either two sweat $Cl^-$ values >60 mM or two disease-causing CF transmembrane conductance regulator mutations (Rowe et al., N. Engl. J. Med. 352:1992-2001 (2005)). Those CF individuals deemed as having exacerbation (inpatients) and hospitalized had at least three of the following symptoms: increased cough/sputum production, fever, weight loss, tachypnea, findings on chest x-ray consistent with pneumonia, or a 10% or greater drop in pulmonary function testing.

Normal controls. All normal subjects were nonsmoking individuals without known lung disease; sputum was collected via hypertonic saline induction.

Materials. Recombinant MMP-9, MMP-8, MMP-12, CXC receptor Abs and isotype control Ab were purchased from R&D Systems (Minneapolis, Minn.). Recombinant human neutrophil elastase (HNE), HNE-specific inhibitor, MMP-9-specific inhibitor, MMP-8-specific inhibitor, MMP-2-specific inhibitor, and PE inhibitor were purchased from Calbiochem (San Diego, Calif.). PE was purchased from US Biologicals (Swampscott, Mass.). PE substrate was purchased from Chem-Impex (Wood Dale, Ill.). Types I and II collagen were purchased from Sigma-Aldrich (St. Louis, Mo.).

Chemotaxis assay. Chemoattractant is placed in the bottom wells of a 3-µm, 96-well polycarbonate filter plate (Millipore, Billerica, Mass.) in 150 µl of DMEM. Neutrophils ($2\times10^5$) were added in 100 µl of DMEM to the top portion. These were incubated for 1 hour at 37° C. in 5% CO2. The upper portion of the plate was removed and micrographs of the migrated cells were made with an Olympus IX70 microscope.

Enzyme inhibitors. The enzyme inhibitors used are as listed in Table I.

TABLE I

Enzyme Inhibitors

| Enzyme Inhibited | Chemical Composition (Manufacturer) | Specificity | Ref. |
|---|---|---|---|
| PE | Z-prolyl prolinal (Calbiochem, San Diego, CA) | $K_I$ = 500 pM | Bakker et al., Biochem. J. 271: 559-562 (1990) |
| MMP-8 | (3R)-(+)-[2-4-methoxybenzenesulfonyl)-1,2,3,4-tetrahydroisoquinoline-3-hydroxamate] (Calbiochem) | $IC_{50}$ = 4 nM | Matter et al., J. Med. Chem. 42: 1908-20 (2007) |
| MMP-9 | $C_{27}H_{33}N_3O_5S$ (Calbiochem) | $IC_{50}$ = 5 nM | Levin et al., Bioorg. Med. Chem. Lett. 11: 2189-2192 (2001) |
| MMP-2 | cis-9-octadecenoyl-N-hydroxylamide (Calbiochem) | $K_I$ = 1.7 µM | Berton et al., J. Biol. Chem. 276: 20458-465 (2007) |
| HNE | N-(2-(4-(2,2-dimethylpropionyloxy) phenylsulfonylamino)benzoyl) aminoacetic acid N-(o-(p-pivaloyloxybenzene) sulfonylaminobenzoyl) glycine (Calbiochem) | $IC_{50}$ = 50 nM | Kawabata et al., Biocehm. Biophys. Res. Commun. 177: 814-20 (1991) |
| Nonspecific MMP | Doxycycline (Calbiochem) | Nonspecific MMP inhibitor | Emingil et al., J. Periodontol. 75: 106-115 (2004) |

Electrospray ionization liquid chromatography-MS/MS. (ESI-LC/MS/MS) for PGP detection PGP and N-α-PGP were measured for in vitro and sputum samples using a MDS Sciex (Applied Biosystems, Foster City, Calif.) API-4000 spectrometer equipped with a Shimadzu HPLC. HPLC was done using a 2.1×150-mm Develosi C30 column (with buffer A: 0.1% formic acid, and buffer B: acetonitrile plus 0.1% formic acid); at 0-0.6 min, 80% buffer A/20% buffer B and at 0.6-5 min, the gradient is up to 0% buffer A/100% buffer B. Background was removed by flushing with 100% isopropanol plus 0.1% formic acid. Positive electrospray mass transitions were at 270-70 and 270-116 for PGP and 312-140 and 312-112 for N-α-PGP.

In vivo murine administration. Mice underwent intratracheal protease administration as described in FIG. 5 legend. MMPs were preactivated using 1 mM aminophenylmercuric acetate for 2 hours at 37° C. The concentrations of proteases administered were: MMP-8, MMP-9, and MMP-12: 55.6 µg/kg; HNE: 200 µg/kg; and PE: 18.4 mg/kg. The relative enzyme activities are: PE enzyme activity: 1 unit=1 µM p-nitroaniline (pNA)/min at 30° C., pH 7; sp. act, 22.6 U/mg PE; MMP-9 enzyme activity: 10 µM ES001 (substrate) and 20 ng of MMP-9=1300 pmol/min per µg at 37° C.; MMP-8 enzyme activity: 10 µM ES 001 (substrate) and 50 ng of MMP-8=250 pmol/min per µg at 37° C.; MMP-12 enzyme activity: 10 µM ES 001 (substrate) and 20 ng of MMP-12=500 pmol/min per µg at 37° C.; and HNE enzyme activity: 22 U/mg protein. (1 unit=hydrolysis of 1.0 µmol pNA/min at 25° C., pH 8.0.

Bronchoalveolar lavage. After mice were euthanized with phenobarbital, mice underwent bilateral thoracotomy and were lavaged with four 1-ml aliquots of cold PBS.

Sputum processing. Sputum was obtained by spontaneous expectoration. Sputum was collected on ice and diluted ½ with 0.9% normal saline, centrifuged at 1000 rpm for 15 min, and supernatant was collected. Protein concentration was measured and then separate aliquots were saved for measurements (MMP, HNE, PE) and MS (N-α-PGP/PGP).

PE activity assay. Twenty microliters of sputum was incubated with a specific substrate (2 mM Z-glycine-proline-pNA) at 37° C. and 5% $CO_2$ and cleavage of pNA) from the substrate by PE was detected using a spectrophotometer at 410 nm and compared with a generated standard curve for PE activity.

Ex vivo collagen assay. One hundred microliters of saline-diluted sputum was incubated with extensively dialyzed, intact type I or II collagen (50 µl, 1 mg/ml) for 24 h at 37° C. and 5% $CO_2$. The samples were filtered through a 10-kDa filter, washed with 20 µl of 1 N HCl, and analyzed using ESI-LC-MS/MS for levels of PGP and N-αPGP. Amounts of PGP and N-α-PGP generated by each sputum sample were determined by subtracting basal levels already present in each sample.

Thereafter, CF sputum samples were individually evaluated and the most active samples were pooled. For the inhibitor experiments, these pooled sputa were treated with noted inhibitor and allowed to incubate for 6 h. At 6 h, dialyzed collagen was added to the sample and sample was further incubated for 18 h. Inhibitor concentrations used were: MMP-8, -9, and -2 at 50 µM, PE at 100 µM, and doxycycline at 1 mM.

Statistical testing. Descriptive statistics including mean and SEM were made for all quantitative measures. The two-tailed Student t test was used for comparisons between two groups and ANOVA was used for comparing means of three or more groups. Pearson's correlation was used to compare the relationship between 1) PE activity and PGP generation, 2) change in FEV1 and change in PGP levels, and 3) change in FVC and change in the PGP (4) relationship between PGP and N-α-PGP in clinical CF samples. Means presented are ±SEM; statistical significance is considered for p<0.05. Calculations were made using Instat software (GraphPad) and SPSS version 14. Values of p<0.05 were determined to be statistically significant.

Results

PGP acts via CXC receptors to induce neutrophil chemotaxis. PGP has been characterized as a neutrophil chemoattractant in a murine model of airway inflammation (Malik et al., *J. Immunol.* 178:1013-1020 (2007)). However, it is unknown whether this nonacetylated peptide acts through similar mechanisms as N-α-PGP. To test this possibility, mAbs were used to block CXCR1 and CXCR2 on neutrophils. When neutrophil migration is examined via chemotaxis assay, either a CXCR1 or CXCR2 Ab used individually causes only a partial reduction in chemotaxis. However, when both Abs are used in conjunction, there is a dose-dependent effect leading to complete blockade of neutrophil influx (FIG. 1A). Isotype-matched control mAb was without effect. Thus, as with N-α-PGP, PGP apparently acts through CXCR1- and CXCR2-dependent mechanisms to induce neutrophil chemotaxis.

N-α-PGP and PGP are elevated in sputum from CF individuals. To examine N-α-PGP and PGP in sputum from CF individuals and normal controls, an MS technique of ESI LCMS/MS was modified for simultaneous detection of these peptides in clinical samples. These clinically stable CF patients (60% female/40% males; mean age, 26.6 years) had moderately severe lung disease with mean forced expiratory volume 1 s (FEV1) of 34% predicted and a mean forced vital capacity (FVC) of 45% of predicted. The majority of these individuals were either ΔF508 heterozygous (40%) or homozygous (50%). Eighty percent of these individuals were *Pseudomonas aeruginosa*-positive via sputum culture.

Figure 1B:
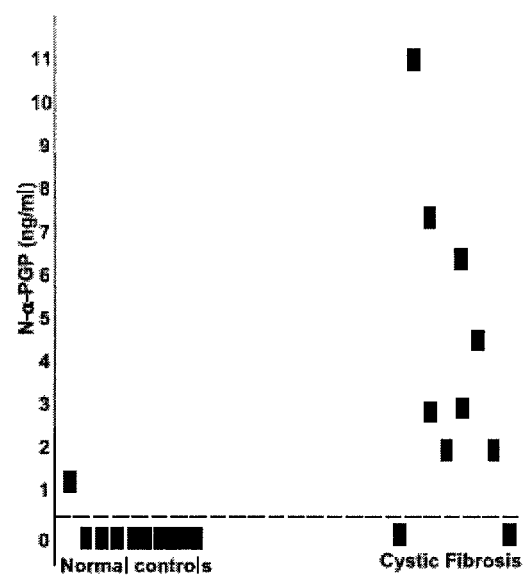
FIG. 1B shows N-$\alpha$-PGP is increased in CF samples compared with normal control samples. CF (n=10) and normal control (n=10) sputum samples were analyzed using ESI-LC/MS/MS for N-$\alpha$-PGP detection. CF samples demonstrated 8 of 10 (80%) positive for N-$\alpha$-PGP vs normal controls having 1 of 10 (10%) positive for N-$\alpha$-PGP. The threshold for positivity (0.825 ng/ml) was determined as two SDs above mean (95% confidence interval) for control sputum values.

FIG. 1B shows that 8 of 10 (80%) CF sputum samples had N-α-PGP above our threshold for positivity vs 1 (10%) 10 normal controls with mean values of each group 3.78 ng/ml (±1.84) and 0.13 ng/ml (±0.12), respectively (p<0.01). The mean values for PGP in the CF samples were 204.8 ng/ml (±83.9) vs 16.2 ng/ml (±19.8) in normal controls (p<0.05), highlighting an elevation of PGP-containing peptides seen in the CF population. These samples demonstrated a correlation coefficient ($R^2$) of 0.76 between their N-α-PGP and PGP levels (p<0.01), demonstrating a strong relationship of the presence of these peptides in clinical samples. The above results led to an inquiry regarding the specific proteases involved in the generation of PGP in vivo.

PE activity is elevated in CF sputum and correlates with PGP. The enzyme directly capable of cleaving PGP from the often repeated "PPGP" motif in collagen is PE, a serine protease which provides specific cleavage at the C-terminal side of a proline. PE is an enzyme implicated in neuropeptide processing and specific neurological conditions. This enzyme has also been reported previously in human T cells. Although its location has been reported to be cytosolic, many reports also describe extracellular activity of the enzyme. This enzyme has been previously identified in lung parenchyma, pulmonary macrophages, and bronchoalveolar lavage fluid.

Figure 2A:
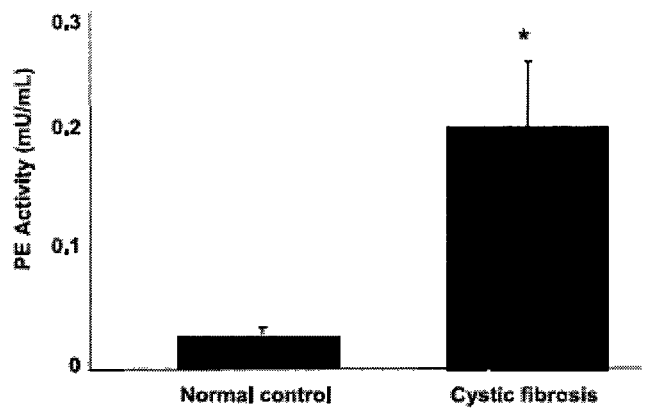
FIG. 2A shows PE activity was elevated in CF samples compared with normal controls. CF (n=10) and normal control (n=10) sputum samples were examined for PE activity using a colorimetric assay. CF samples demonstrated a 5-fold increase in PE activity compared with normal controls (*, p<0.01).

To determine whether PE may be playing a role in PGP generation in the CF lower airway, its presence was assayed in CF sputum. Using a very specific substrate for PE (Z-glycineproline-pNA), a 5-fold increase in PE activity was observed in CF patients (n=10) compared with normal control samples (FIG. 2A) (n=10). When PGP production and PE activity was correlated in the CF samples capable of generating PGP (n=8), the correlation coefficient ($R^2$) was 0.72

Figure 2B:
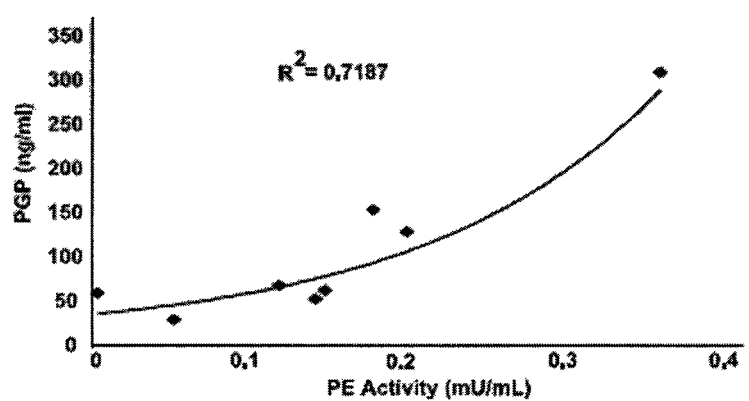
FIG. 2B shows the concentration of PGP was correlated with PE activity in CF samples (n=8). The samples demonstrated a correlation coefficient ($R^2$) of 0.718 (p<0.01).

(FIG. 2B; p<0.01). Together, these results show increased PE activity with PGP generation in vivo. However, PE is only capable of cleaving substrates 30-100 aa or less; therefore, PE alone could not directly cleave collagen to a tripeptide and would require an initial cleavage of collagen before liberating PGP. Therefore, PGP generation from intact collagen is a stepwise process involving initial proteolytic cleavage of collagen with subsequent activity by PE.

Figures 3A, 3B:
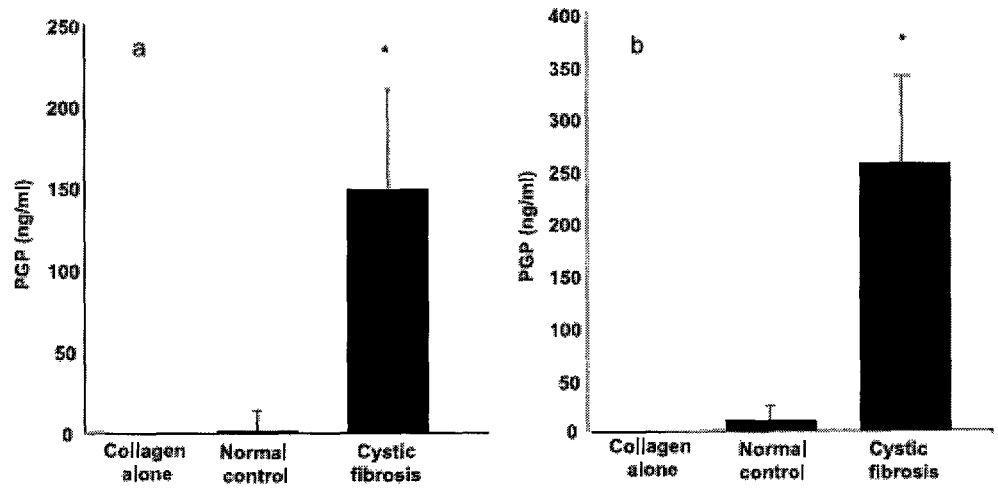
FIG. 3A shows PGP production was significantly increased in CF samples compared with normal control samples on type I collagen. CF sputum (n=10) and normal control sputum (n=10) were each incubated on extensively dialyzed type I collagen for 24 h at 37° C. PGP values of the samples on PBS were subtracted from PGP values of samples incubated on type I collagen to determine PGP production. PGP generated from CF samples were significantly increased compared with normal control samples on type I collagen (*, p<0.05).
FIG. 3B shows PGP production was significantly increased in CF samples compared with normal control samples on type II collagen. CF sputum (n=10) and normal control sputum (n=10) were each incubated on extensively dialyzed type II collagen for 24 h at 37° C. PGP values of the samples on PBS were subtracted from PGP values of samples incubated on type II collagen to determine PGP production. PGP generated from CF samples were significantly increased compared with normal control samples on type II collagen (*, p<0.05).

CF sputum is capable of generating PGP from collagen. Increased protease activity in CF sputum has been reported; human neutrophil elastase (HNE) was elevated along with the MMP isoforms collagenase-2 (MMP-8), gelatinase B (MMP-9), stromelysin-3 (MMP-11), and macrophage metalloelastase (MMP-12) (Gaggar et al., *Am. J. Physiol.* 293:L96-L104 (2007)). Since these enzymes and PE were found to have elevated activity in CF sputum, CF sputum was hypothesized to have the necessary components to generate PGP from collagen. Type I collagen was used for these studies, because this is the prominent form of collagen seen in the airways. However, to demonstrate the potential generalizability of this process, type II collagen was also examined. Both CF and normal control sputum samples were incubated with either type I or type II collagen and examined via MS for PGP or N-α-PGP. FIG. 3A shows that sputum samples from CF individuals generated PGP from type I collagen (average, 148 ng/ml; range, 130-530% of basal PGP) compared with normal patient samples (average, 1.3 ng/ml; range, 0-117% of basal PGP; p<0.05). Similarly, FIG. 3B demonstrates CF sputum samples generated PGP from type II collagen (average, 240 ng/ml; range, 140-675% of basal PGP) compared with PGP generation from normal controls (average, 9.8 ng/ml; range. 0-155% of basal PGP; p<0.05). Slightly lower but statistically significant increases in N-α-PGP levels were seen in CF sputum incubated with both type I and type II collagen. These data demonstrate that CF sputum contains the proteolytic enzymes necessary to generate PGP from collagen.

Figure 4:
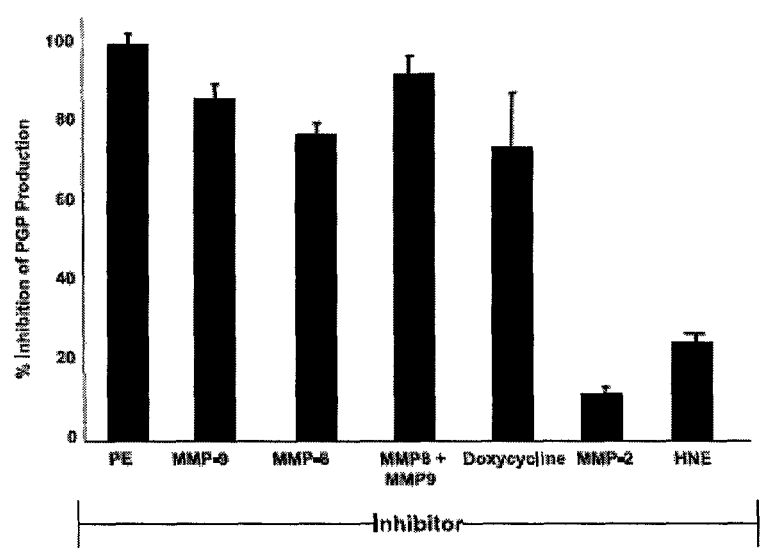
FIG. 4 shows PE, MMP-8, and MMP-9 inhibitors block the production of PGP. Inhibitors were incubated for 6 h with pooled CF sputum and these sputa were placed on type I collagen for 24 h as previously described. PGP concentrations from these groups were compared with pooled CF sputum on type I collagen not treated with inhibitor. PE inhibitor demonstrated complete blockade of PGP production and MMP-8- and -9-specific inhibitors individually demonstrated 80-90% inhibition, with their combination resulting in complete blockade of PGP generation. Doxycycline, a nonspecific MMP inhibitor, demonstrated comparable PGP inhibition as MMP-8 alone. Neither MMP-2-nor HNE-specific inhibitors resulted in significant changes in PGP production.

PGP generation is significantly abrogated by use of specific protease inhibitors. To identify the specific proteases involved in PGP generation, the CF sputum was used in an ex vivo assay for PGP production from intact collagen in the presence of various protease inhibitors. CF sputum was incubated with known specific enzyme inhibitors and then incubated with type I collagen. The results were reported as percent inhibition compared with PGP generation by CF sputum alone (FIG. 4). PE inhibition completely blocked generation of PGP, indicating its central importance to PGP generation. PGP production was also significantly inhibited by both MMP-8 and MMP-9 antagonists individually, and this inhibition is augmented when MMP-8 and MMP-9 antagonists were combined. That MMP-8 and -9 inhibitors alone block PGP production showed that the two proteases act in concert to generate an optimal substrate for PE. MMP-2 and human neutrophil elastase (HNE) inhibitors had minimal effects on PGP generation. Doxycycline, a clinically used antimicrobial which also acts as a nonspecific small molecule MMP inhibitor, caused 75% inhibition of PGP production. To confirm the implied role for MMP-8, MMP-9, and PE in PGP generation by CF sputum, such PGP production was recapitulated by in vivo administration of proteases into murine airways.

Figure 5A:
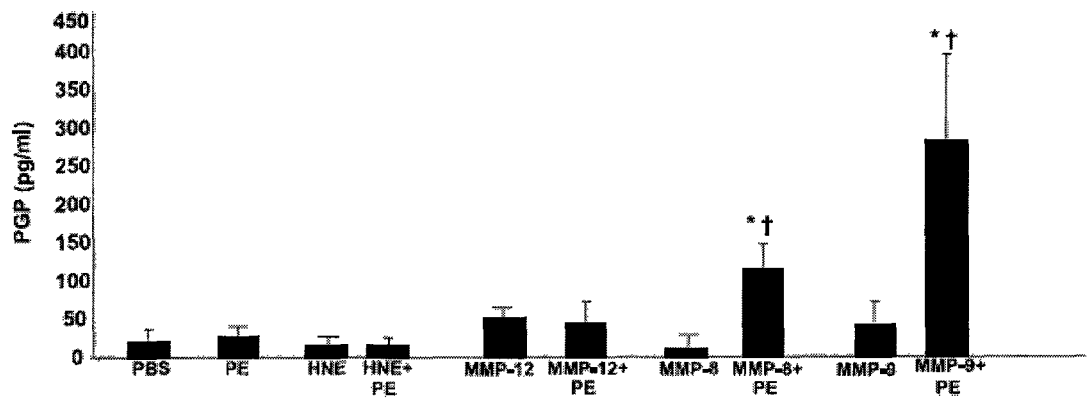
FIG. 5A shows in vivo PGP generation. In vivo PGP production was examined using MMPs or human neutrophil elastase (HNE) with or without PE. Various proteases (50 µl) were administered intratracheally into murine (4- to 6-wk-old BALB/c mice) airways and bronchoalveolar lavage fluid was collected 24 h later. PGP levels were determined using ESI LC-MS/MS. PGP production was significantly increased in MMP-9 with PE (*, p<0.05 vs PBS control; †, p<0.05 vs MMP-9 alone) and MMP-8 with PE (*, p<0.05 vs PBS control; †, p<0.05 vs MMP-8 alone) compared with other proteases with or without PE. PBS control and PE alone had similar PGP production. Aminophenylmercuric acetate alone (or in combination with PE) also did not generate PGP. Number of mice per group=6.
Figure 5B:
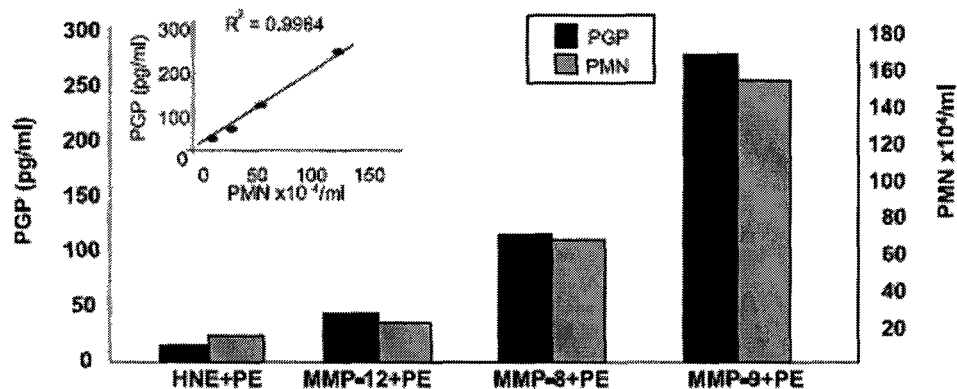
FIG. 5B shows PGP production correlated with neutrophil influx. PGP production levels (■) were compared with PMN counts (▨) in mice treated with a combination of the indicated protease and PE from FIG. 3A. There was a notable correlation between PGP production and PMN counts for each condition ($R^2=0.996$, inset).

PGP generation correlates with polymorphonuclear leukocyte/neutrophil (PMN) influx and is found to be a stepwise process involving MMPs and PE. FIG. 5A shows that following intratracheal delivery to murine lungs, MMPs alone, HNE alone, or PE alone did not generate PGP. However, when either MMP-8 or MMP-9 was combined with PE, PGP was generated at levels significantly higher than PBS control or either enzyme alone. Of note, MMP-12 and HNE, two prominent proteases found in a variety of chronic neutrophilic lung diseases including CF, generated no PGP in the presence of PE. FIG. 5B demonstrated a tight correlation ($R^2=0.996$) between PMN influx and PGP generation following exposure to enzyme combinations. These results verified the stepwise generation of PGP with specific MMPs in combination with PE and completely recapitulated our ex vivo human findings.

PGP serves as a unique biomarker during CF exacerbation. The presence of PGP in CF secretions led to the question of whether this peptide may serve as a novel inflammatory biomarker in CF lung disease. PGP measurements were taken in CF inpatients at the beginning of CF exacerbation (within 48 h of admission) and at the end of hospitalization (day 13/14). All subjects were treated with standard CF inpatient therapy (including two antibiotics (aminoglycoside and either β-lactam or fluoroquinolone), intensive airway clearance techniques, and nebulized therapies (i.e., recombinant human DNase, albuterol) during the hospitalization. These patients were 60% female, 40% male, and had a mean age of 18 years. These individuals were either ΔF508 heterozygous (33%) or homozygous (66%). Eighty-three percent of these individuals were *P. aeruginosa*-positive via sputum culture. They also demonstrated moderately severe lung disease at admission (mean FEV1=43% of predicted and mean FVC=60% of predicted) which improved after inpatient therapy (mean FEV1=51% of predicted and mean FVC=67% of predicted).

Figure 6:
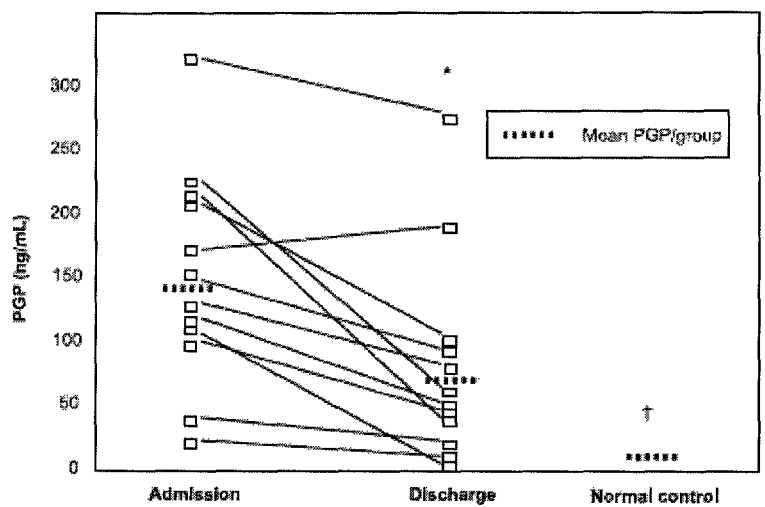
FIG. 6 shows PGP levels declined during inpatient therapy for CF exacerbation. Sputum PGP levels from CF individuals (n=12) were examined within 48 h of admission and at discharge (day 13/14) for CF exacerbation. The mean levels of PGP decreased during hospitalization (146.4±24.4 vs 80.0±22.5; *, p<0.01), although these levels are still 5-fold elevated compared with secretions from normal controls (†, p<0.01).
Figure 7:
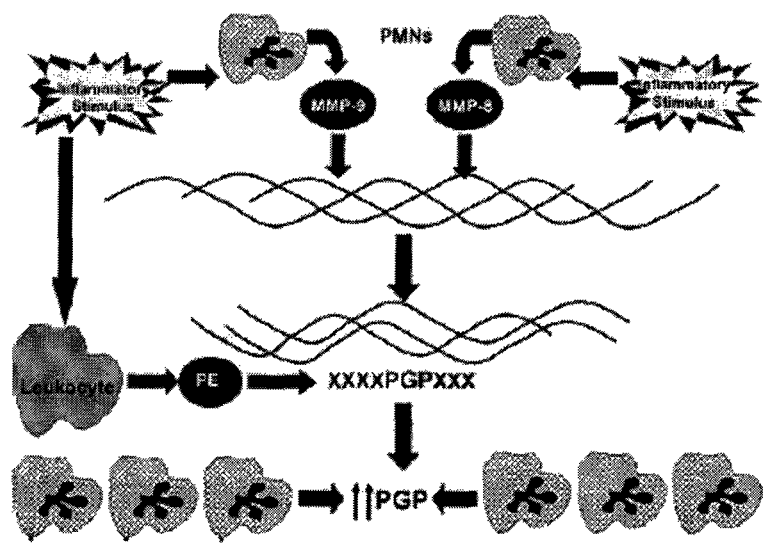
FIG. 7 is a schematic showing PGP generation is a multi-step process. The generation of PGP is a multistep process initially involving release of MMP-8 or MMP-9 from activated neutrophils. These proteases denature and proteolytically cleave collagen to fragments 30-100 amino acids (aa) in length. These collagen fragments are then further cleaved to PGP by PE. The PGP generated then acts as a neutrophil chemoattractant and allows for an environment of ongoing proteolytic damage and PGP generation.

FIG. 6 shows a significant reduction in the PGP levels during the course of hospitalization in aggregate and a notable decline in 11 of the 12 subjects (p<0.01).

There was a correlation seen in decline of PGP levels with improvement in FEV1 and FVC during hospitalization and these results trended toward statistical significance (R=0.53 for FEV1 and PGP, p=0.12; R=0.52 for FVC and PGP, p=0.11). Despite the reduction in PGP levels during hospitalization in CF subjects, the PGP levels upon discharge remained 5-fold higher than that seen in normal controls (p<0.01), indicating that even after resolution of CF exacerbation, these patients demonstrated ongoing inflammation and matrix degradation which may be mediated in part by proteases and PGP.

Example 2

In Vitro and Ex Vivo Analysis of S 17092

Neutrophil migration is examined via chemotaxis assay using mouse and human polymorphonuclear neutrophils and HL-60 cell line. A method for measuring neutrophil migration via chemotaxis assay is described above. Specifically, neutrophil migration is examined in the presence or absence of 1 mg, 2 mg, 3 mg, 4 mg or 5 mg S17092 and PGP. S 17092 inhibits neutrophil migration.

Example 3

In Vivo Analyses of S 17092

To confirm the role of S 17092 in vivo, neutrophilic influx to the lungs of mice exposed to LPS intratracheally is determined in the presence or absence of S 17092. Specifically, LPS is administered intratracheally to mice followed by administration of a daily dose of 10 mg/kg or 30 mg/kg of S 17092. Neutrophilic influx is determined as described above. Neutrophilic influx is reduced by S 17092.

In addition, neutrophilic influx and PGP generation in mice exposed to viral and bacterial infections is determined in the presence or absence of S 17092. Specifically, neutrophilic influx and PGP levels are determined in mice with a viral or bacterial infection. Such mice are then administered daily dose of 10 mg/kg or 30 mg/kg of S 17092 followed by re-evaluation of neutrophilic influx and PGP levels. Neutrophilic influx and PGP levels is reduced by administration of S 17092.

What is claimed is:

1. A method for reducing neutrophilic inflammation in a subject comprising:
   (a) selecting a subject with neutrophilic inflammation; and
   (b) administering to the subject an agent that inhibits the expression or activity of prolyl endopeptidase, wherein the agent that inhibits the expression or activity of prolyl endopeptidase is selected from the group consisting of a proline derivative, a pyrrolidineamide derivative, a prolinal derivative, a sulfated chitooligosaccharide, a plant phenolic, eurystatin, an inhibitory peptide, and an inhibitory nucleic acid, wherein, if the agent is a plant phenolic, the plant phenolic is selected from the group consisting of 1,2,3-trigalloyl glucopyranoside, 1,2,6-trigalloyl glucopyranoside, 1,2,3,4,6- pentagalloyl glucopyranoside, 1,2,6-trigalloyl alloside, 1,3,6-trigalloyl alloside, 1,2,3,6-tetragalloyl alloside, acetonyl geraniin, corilagin, elaeocarpusin, euphorscopin, geraniin, helioscopin B, helioscopinin A, helioscopinin B, jolkinin, macranganin, rugosin E, supinanin, and teracatain.

2. The method of claim 1, wherein the agent is Z-prolyl prolinal or JTP-4819.

3. The method of claim 1, wherein the agent is an inhibitory peptide.

4. The method of claim 3, wherein the inhibitory peptide is SNA-115 or SNA-115T.

5. The method of claim 1, wherein the agent is an inhibitory nucleic acid.

6. The method of claim 5, wherein the inhibitory nucleic acid is selected from the group consisting of an antisense molecule, aptamer, ribozyme, triplex forming molecule, short interfering RNA (siRNA), and external guide sequence.

7. The method of claim 1, wherein the agent is administered by oral inhalation, nasal inhalation, or intranasal mucosal administration.

8. The method of claim 1, wherein the subject has a disease associated with neutrophilic inflammation, wherein the disease is selected from the group consisting of asthma, chronic obstructive pulmonary disease (COPD), cystic fibrosis (CF), pulmonary transplantation rejection, chronic bronchitis, emphysema, bronchiectasis, bronchiolitis obliterans syndrome (BOS), interstitial pneumonia, and pulmonary fibrosis.

9. The method of claim 1, wherein the subject has a disease associated with neutrophilic inflammation, wherein the disease is bacterial infection or viral infection.

10. The method of claim 9, wherein the bacterial infection is a bacterial lung infection.

11. The method of claim 9, wherein the viral infection is a viral lung infection.

12. The method of claim 8, wherein the disease is COPD.

13. The method of claim 8, wherein the disease is cystic fibrosis.

14. The method of claim 1, further comprising administering to the subject a second therapeutic agent, wherein the second therapeutic agent is selected from the group consisting of a matrix metalloprotease (MMP) inhibitor, an anti-inflammatory agent, an anti-microbial agent, and an anti-viral agent.

15. The method of claim 14, wherein the second therapeutic agent is a matrix metalloprotease (MMP) inhibitor.

16. The method of claim 15, wherein the matrix metalloprotease is MMP-8 or MMP-9.

17. A method of treating neutrophilic inflammation or a disease associated with neutrophilic inflammation in a subject, comprising:
   (a) obtaining a biological sample from the subject; and
   (b) determining the level of expression or activity of PE in the sample, wherein an increase in expression or activity of PE as compared to a control indicates the subject has neutrophilic inflammation or a disease associated with neutrophilic inflammation; and
   (c) administering to the subject an agent that inhibits the expression or activity of prolyl endopeptidase if the subject has neutrophilic inflammation or a disease associated with neutrophilic inflammation, wherein the agent that inhibits the expression or activity of prolyl endopeptidase is selected from the group consisting of a proline derivative, a pyrrolidineamide derivative, a prolinal derivative, a sulfated chitooligosaccharide, a plant phenolic, eurystatin, an inhibitory peptide, and an inhibitory nucleic acid.

18. The method of claim 17, wherein the biological sample is a biological fluid.

19. The method of claim 18, wherein the biological fluid is selected from the group consisting of serum, sputum and lung lavage.

20. The method of claim 17, wherein the determining step is carried out using an immunological method.

21. The method of claim 17, wherein the agent is S 17092.

22. The method of claim 17, wherein the agent is a plant phenolic.

23. The method of claim 22, wherein the plant phenolic is selected from the group consisting of 1,2,3-trigalloyl glucopyranoside, 1,2,6-trigalloyl glucopyranoside, 1,2,3,4,6-pentagalloyl gluco-pyranoside, 1,2,6-trigalloyl alloside, 1,3,6-trigalloyl alloside, 1,2,3,6-tetragalloyl alloside, acetonyl geraniin, corilagin, elaeocarpusin, euphorscopin, geraniin, helioscopin B, helioscopinin A, helioscopinin B, jolkinin, macranganin, rugosin E, supinanin, and teracatain.

24. The method of claim 17, wherein the agent is Z-prolyl prolinal or JTP-4819.

25. The method of claim 17, wherein the agent is an inhibitory peptide.

26. The method of claim 25, wherein the inhibitory peptide is SNA-115 or SNA-115T.

27. The method of claim 17, wherein the agent is an inhibitory nucleic acid.

28. The method of claim 27, wherein the inhibitory nucleic acid is selected from the group consisting of an antisense molecule, aptamer, ribozyme, triplex forming molecule, short interfering RNA (siRNA), and external guide sequence.

* * * * *